(12) United States Patent
Roelants et al.

(10) Patent No.: US 12,110,527 B2
(45) Date of Patent: Oct. 8, 2024

(54) PRODUCTION OF SYMMETRICAL BOLAFORM SOPHOROSIDES

(71) Applicants: UNIVERSITEIT GENT, Ghent (BE); AMPHISTAR, Lievegem (BE)

(72) Inventors: Sophie Roelants, Melle (BE); Lisa Van Renterghem, Evergem (BE); Wim Soetaert, Lievegem (BE); Jelle Remmery, Ghent (BE)

(73) Assignees: UNIVERSITEIT GENT, Ghent (BE); AMPHISTAR, Lievegem (BE)

( * ) Notice: Subject to any disclaimer, the term of this patent is extended or adjusted under 35 U.S.C. 154(b) by 731 days.

(21) Appl. No.: 17/292,092

(22) PCT Filed: Nov. 21, 2019

(86) PCT No.: PCT/EP2019/082063
§ 371 (c)(1),
(2) Date: May 7, 2021

(87) PCT Pub. No.: WO2020/104582
PCT Pub. Date: May 28, 2020

(65) Prior Publication Data
US 2022/0033869 A1 Feb. 3, 2022

(30) Foreign Application Priority Data
Nov. 22, 2018 (EP) .................................. 18207793

(51) Int. Cl.
| | | |
|---|---|---|
| *C12P 19/44* | (2006.01) | |
| *C12N 9/02* | (2006.01) | |
| *C12N 9/04* | (2006.01) | |
| *C12N 15/01* | (2006.01) | |
| *C12P 1/02* | (2006.01) | |
| *C12P 7/6436* | (2022.01) | |

(52) U.S. Cl.
CPC ............ *C12P 19/44* (2013.01); *C12N 9/0006* (2013.01); *C12N 9/0071* (2013.01); *C12N 15/01* (2013.01); *C12Y 101/0302* (2013.01); *C12Y 114/14001* (2013.01)

(58) Field of Classification Search
None
See application file for complete search history.

(56) References Cited

U.S. PATENT DOCUMENTS

| | | |
|---|---|---|
| 2013/0059341 A1 | 3/2013 | Ikushiro et al. |
| 2013/0089892 A1 | 4/2013 | Soetaert et al. |
| 2016/0168612 A1 | 6/2016 | Soetaert et al. |
| 2016/0304913 A1 | 10/2016 | Gatter et al. |

FOREIGN PATENT DOCUMENTS

| | | |
|---|---|---|
| JP | 2015123019 A | 7/2015 |
| WO | 2011-154523 A1 | 12/2011 |
| WO | 2015-028278 A1 | 3/2015 |

OTHER PUBLICATIONS

Claus et al., "Sophorolipid production by yeasts: a critical review of the literature and suggestions for future research", Applied Microbiology and Biotechnology, vol. 101, pp. 7811-7821 (Year: 2017).*
China National Intellectual Property Administration, "First Notification of Office Action", issued in Chinese Patent Application No. 2019800766806, which is a counterpart to U.S. Appl. No. 17/292,092, on Aug. 30, 2023, 16 pages (8 pages of English Translation of Office Action and 8 pages of original Office Action).
Japanese Office Action as Issued on Nov. 8, 2023 in Respect to Counterpart Japanese Patent Application No. 2021-529127 and its English Translation.
International Search Report and Written Opinion dated Feb. 21, 2020 from PCT International Appln. No. PCT/EP2019/082063.
Van Bogaert et al., "The Biosynthetic Gene Cluster for Sophorolipids: A Biotechnological Interesting Biosurfactant Produced By Starmerella bombicola," Molecular Microbiology, vol. 88, No. 3, Mar. 21, 2013, pp. 501-509.
Van Renterghem et al., "From Lab to Market: An Integrated Bioprocess Design Approach for New-to-Nature Biosurfactants Produced by Starmerella bombicola," Biotechnology and Bioengineering, vol. 115, No. 5, Feb. 4, 2018, pp. 1195-1206.
Lodens et al., "Transformation of an Exotic Yeast Species Into A Platform Organism: A Case Study for Engineering Glycolipid Production in the Yeast *Starmerella bombicola*," Synthetic Biology: Methods and Protocols, Methods in Molecular Biology, Part of Springer Nature 2018, vol. 1772, Chapter 5, pp. 95-123.
Geys et al., "Increasing Uniformity of Biosurfactant Production in Starmerella bombicola Via the Expression of Chimeric Cytochrome P450s," Colloids and Interfaces, vol. 2, No. 42, Oct. 3, 2018, 13 pages.

(Continued)

*Primary Examiner* — Michelle F. Paguio Frising
(74) *Attorney, Agent, or Firm* — Amster, Rothstein & Ebenstein LLP

(57) ABSTRACT

The present invention relates to the field of microbial production of novel biosurfactants. More specifically, the present invention discloses the usage of a fungal strain such as the yeast *Starmerella bombicola* having a dysfunctional CYP52M1 cytochrome P450 monooxygenase and a dysfunctional FAO1 fatty alcohol oxidase for producing high amounts of so-called "symmetrical bolaform sophorosides" where both sophorose moieties are attached through a terminal glycosidic linkage to the hydrophobic linker. In addition, the present invention further discloses that the latter yeast can also be used to produce alkyl sophorosides and symmetrical bolaform glucosides.

13 Claims, 9 Drawing Sheets

Specification includes a Sequence Listing.

(56) References Cited

OTHER PUBLICATIONS

Takahashi et al., "Identification of the Fatty Alcohol Oxidase FAO1 from Starmerella bombicola and Improved Novel Glycolipids Production in an FAO1 Knockout Mutant," Appl. Microbiol. Biotechnol., vol. 100, Jul. 6, 2016, pp. 9519-9528.

Van Bogaert et al., "Microbial Synthesis of Sophorolipids," Process Biochemistry, vol. 46, 2011, pp. 821-833.

Roelants et al., "Candida bombicola as a Platform Organism for the Production of Tailor-Made Biomolecules," Biotechnology and Bioengineering, vol. 110, No. 9, May 1, 2013, pp. 2494-2503.

* cited by examiner

SEQUENCE LISTING

```
<160> NUMBER OF SEQ ID NOS: 20

<210> SEQ ID NO 1
<211> LENGTH: 26
<212> TYPE: DNA
<213> ORGANISM: Artificial sequence
<220> FEATURE:
<223> OTHER INFORMATION: Primer

<400> SEQUENCE: 1
```
aaggcgggct ggaatgcata tctgag                                            26

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
gatgtcgaat agccgggctg ctac                                              24

<210> SEQ ID NO 3
<211> LENGTH: 24
<212> TYPE: DNA
<213> ORGANISM: Artificial sequence
<220> FEATURE:
<223> OTHER INFORMATION: Primer

<400> SEQUENCE: 3
aagaacatcg attttccatg gcag                                              24

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
cgactcacta tagggagagc ggc                                               23

<210> SEQ ID NO 5
<211> LENGTH: 40
<212> TYPE: DNA
<213> ORGANISM: Artificial sequence
<220> FEATURE:
<223> OTHER INFORMATION: Primer

<400> SEQUENCE: 5
ctcgagtttt tcagcaagat tgccaagtcg ttcaacacag                             40

<210> SEQ ID NO 6
<211> LENGTH: 40
<212> TYPE: DNA
<213> ORGANISM: Artificial sequence
<220> FEATURE:
<223> OTHER INFORMATION: Primer

<400> SEQUENCE: 6
aggagatctt ctagaaagat ctgagacagc agcttgtcac                             40

<210> SEQ ID NO 7
<211> LENGTH: 42
<212> TYPE: DNA
<213> ORGANISM: Artificial sequence
<220> FEATURE:
<223> OTHER INFORMATION: Primer

<400> SEQUENCE: 7
gtgacaagct gctgtctcag atctttctag aagatctcct ac                          42

<210> SEQ ID NO 8
<211> LENGTH: 45
<212> TYPE: DNA
<213> ORGANISM: Artificial sequence

```
<220> FEATURE:
<223> OTHER INFORMATION: Primer

<400> SEQUENCE: 8
ctgtgttgaa cgacttggca atcttgctga aaaactcgag ccatc          45

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
tgccaagtcg ttcaacacag                                       20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
ctgagacagc agcttgtcac                                       20

<210> SEQ ID NO 11
<211> LENGTH: 28
<212> TYPE: DNA
<213> ORGANISM: Artificial sequence
<220> FEATURE:
<223> OTHER INFORMATION: Primer

<400> SEQUENCE: 11
gccttggcat tcaacatctc agggaatc                              28

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gcacgccctt agcttcagag                                       20

<210> SEQ ID NO 13
<211> LENGTH: 40
<212> TYPE: DNA
<213> ORGANISM: Artificial sequence
<220> FEATURE:
<223> OTHER INFORMATION: Primer

<400> SEQUENCE: 13
gactgagatg acggaagagg cccgaacata ccagtttcgc                 40

<210> SEQ ID NO 14
<211> LENGTH: 40
<212> TYPE: DNA
<213> ORGANISM: Artificial sequence
<220> FEATURE:
<223> OTHER INFORMATION: Primer

<400> SEQUENCE: 14
aagcttagtg agatccgcgt gaacaaacga cccaacaccc                 40
```

```
<210> SEQ ID NO 15
<211> LENGTH: 41
<212> TYPE: DNA
<213> ORGANISM: Artificial sequence
<220> FEATURE:
<223> OTHER INFORMATION: Primer

<400> SEQUENCE: 15
gggtgttggg tcgtttgttc acgcggatct cactaagctt c          41

<210> SEQ ID NO 16
<211> LENGTH: 40
<212> TYPE: DNA
<213> ORGANISM: Artificial sequence
<220> FEATURE:
<223> OTHER INFORMATION: Primer

<400> SEQUENCE: 16
gcgaaactgg tatgttcggg cctcttccgt catctcagtc            40

<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
gccagtgcaa caagtatgag                                  20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
gaccaggcta aacgcatcac                                  20

<210> SEQ ID NO 19
<211> LENGTH: 18
<212> TYPE: DNA
<213> ORGANISM: Artificial sequence
<220> FEATURE:
<223> OTHER INFORMATION: Primer

<400> SEQUENCE: 19
gagagtggga cctgattc                                    18

<210> SEQ ID NO 20
<211> LENGTH: 22
<212> TYPE: DNA
<213> ORGANISM: Artificial sequence
<220> FEATURE:
<223> OTHER INFORMATION: Primer

<400> SEQUENCE: 20
ctgctctcaa caccgagtgt ag                               22
```

PRODUCTION OF SYMMETRICAL BOLAFORM SOPHOROSIDES

CROSS-REFERENCE TO RELATED APPLICATIONS

This application is a U.S. national stage entry under 35 U.S.C. § 371 of PCT International Patent Application No. PCT/EP2019/082063, filed Nov. 21, 2019, which claims priority to European Patent Application No. 18207793.3, filed Nov. 22, 2018, the contents of which are incorporated herein by reference in their entirety.

INCORPORATION BY REFERENCE OF SEQUENCE LISTING

The Sequence Listing entitled "BBEP-002-PCT.txt" (3,818 bytes) created on Nov. 21, 2019 and submitted electronically using the U.S. Patent Center on May 7, 2021 is incorporated by reference as the Sequence Listing for the subject application.

TECHNICAL FIELD OF INVENTION

The present invention relates to the field of microbial production of novel biosurfactants. More specifically, the present invention discloses the usage of a fungal strain such as the yeast Starmerella bombicola having a dysfunctional CYP52M1 cytochrome P450 monooxygenase and a dysfunctional FAO1 fatty alcohol oxidase for producing high amounts of so-called "symmetrical (acetylated) bolaform sophorosides" where both sophorose moieties are connected to the hydrophobic linker by a glycosidic bound. In addition, the present invention further discloses that the latter yeast can also be used to produce (acetylated) alkyl sophorosides.

BACKGROUND ART

It has been demonstrated that the industrial sophorolipid producing yeast Starmerella bombicola can be exploited as a platform organism for the production of glycolipids and other biochemicals (Roelants et al., 2013; Roelants et al., 2016). One of the most recent achievements in this respect, describes the redesigning of this yeast to produce so-called bola sophorosides (SSs) (Van Renterghem et al., 2018) (FIG. 1). These bola SSs are a novel type of glycolipid which provide a more chemically stable alternative to the earlier described bola sophorolipids (SLs) (Soetaert et al., 2013; Van Bogaert et al., 2016). Indeed, Van Renterghem et al. (2018) disclose that a S. bombicola strain deficient in its acetyltransferase (at), lactonase esterase (sble) and alcohol oxidase 1 (fao1) when fed with fatty alcohols produces bola-sophorosides. However, the latter bola-sophorosides comprise-besides bola-sophorosides-still substantial amounts of bolaform sophorolipids. There is thus still a need for further strain improvements in order to shift the bolaform sophorolipid production more towards the sophoroside compounds. Moreover, the bola sophorosides produced by Van Renterghem are a mixture of non-symmetrical i.e. one sophorose moiety is subterminally linked, while the other one is terminally linked and symmetrical bola sophorosides (both sophoroses are terminally linked). The molecules described by Van Renterghem are non-acetylated due to the deletion of the at gene (acetyltransferase).

Takahashi et al. (2016) described the increased production of alkyl sophorosides by a S. bombicola strain having a deleted fao1 gene as compared to the wild type fed with fatty alcohols. However, this increase in production is still accompanied with production of acidic and lactonic sophorolipids, which is undesired.

DESCRIPTION OF INVENTION

Figure 1:
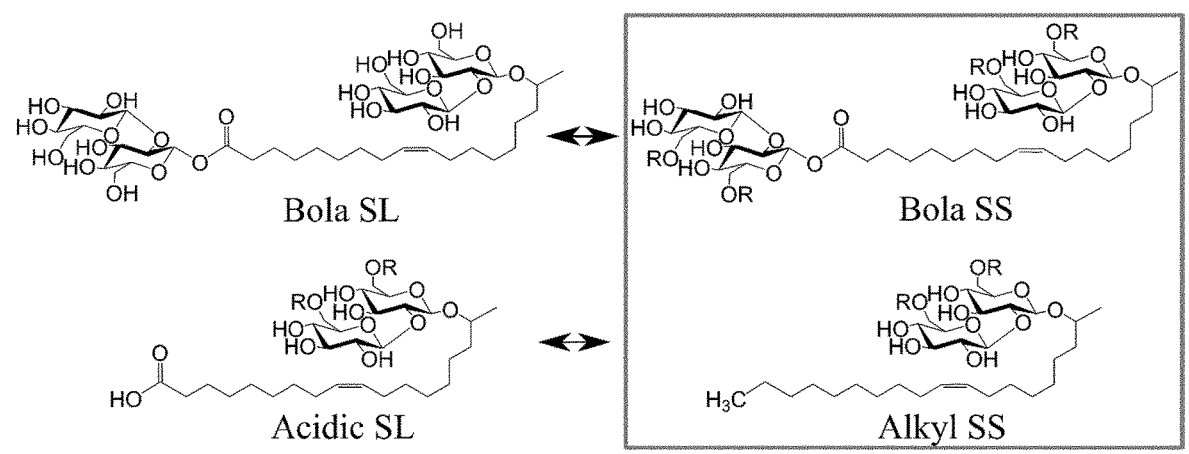
FIG. 1: Chemical structures of sophorolipids (SLs) (left) and sophorosides (SSs) (right, circled in grey). Bola SLs and acidic SLs are presented as a comparison. Glycosidic and ester linkages are indicated to highlight the difference between bola sophorolipids and sophorosides, whereas the methyl group of alkyl SS is indicated to highlight the difference between the acidic SLs having a carboxylic group. R groups represents either an H or acetyl (COCH3) group.

The present invention relates to a method to produce fully symmetrical bola sophorosides which are free from contaminating sophorolipids (acidic, lactonic, bola) comprising feeding a mutated fungal strain such as a *Starmerella bombicola* strain with a fatty alcohol having an aliphatic tail chain length of at least 6 carbons wherein said fungal strain has a dysfunctional CYP52M1 cytochrome P450 monooxygenase and a dysfunctional FAO1 fatty alcohol oxidase.

The term 'a fully symmetrical bola sophoroside' refers to a bola sophoroside (i.e. a sophoroside consisting of two sophorose units located on each side of the fatty hydrophobic linker or aliphatic tail as described by Van Renterghem et al. (2018)) wherein both sophorose entities or units are attached in an exclusively terminal position (w position) on the fatty hydrophobic linker.

The fatty (hydrophobic) linker or aliphatic chain can contain at least 6 (i.e. 6, 7, 8, 9, 10, 11, 12, 13, 14, 15, 16, 17, 18, 19, 20 or more) carbon atoms, can be branched and/or can contain insaturations.

The terms 'free from contaminating sophorolipids' refers to the production of fully symmetrical bola sophorosides wherein no measurable amounts of acidic-bola- and/or lactonic sophorolipids are produced as contaminating by-products.

The term 'fungal strain' refers to any genetic variant or sub-type of a particular fungus, such as a yeast strain, which is capable of producing sophorolipids. In other words, the present invention relates to a usage as described above wherein said fungal strain is a fungal strain capable of producing sophorolipids endogenously or after genetic modification. More specifically, this fungal strain is a fungal species comprising, but not limited to: *Candida apicola* (Gorin et al., 1961) which was initially identified as *C. magnolia*, *C. bombicola* (Spencer et al., 1970), *Wickerhamiella domericqiae* (Chen et al., 2006), *Rhodotorula bogoriensis* (Tulloch et al., 1968), *Candida batistae* (Konishi et al., 2008), *Candida floricola* (Imura et al., 2010), *Candida riodocensis*, *Candida* stellate and *Candida* sp. NRRL Y-27208 (Kurzmanet al., 2010), *Candida kuoi* (Kurtzman, 2012) and any other strain of the *Starmerella* clade. The present invention more specifically relates to a usage as described above wherein said *Starmerella* (*Candida*) *bombicola* is the strain *Starmerella* (*Candida*) *bombicola* ATCC 22214 (CBS 6009) or strains derived thereof.

The terms "a mutated fungal strain" relates to a fungal strain as defined above wherein said strain is mutated so that the enzymes CYP52M1 and FAO1 are non- or dysfunctional. With regard to CYP52M1 this means that no hydroxylation of the fatty alcohol substrate can occur anymore and with regard to FAO1 this means that no oxidation of the OH group present on the fatty alcohol towards the corresponding aldehyde can occur anymore.

The term 'dysfunctional' means in general a gene or protein which is not performing 'normally', and/or, has an absent or impaired function. The term thus refers to a gene or protein which is: a) not functional because it is not present, b) still present but is rendered non-functional or c) which is present but has a weakened or reduced function. The term 'dysfunctional' specifically refers to a gene having lost its capability to encode for the fully functional enzymes CYP52M1 and FAO1, or polypeptides/proteins having lost its CYP52M1 and FAO1 activity, either completely or partially. 'Partially' means that the activity of the latter enzymes—measured by any method known in the art—is significantly lower (p<0.05) when compared to the activity of the wild-type counterparts of said enzymes.

A 'dysfunctional' nucleic acid molecule as defined above can be obtained by mutation or by any known means to silence the transcription or translation of said nucleic acid. The latter means comprise the insertion of a nucleic acid fragment, a marker gene or any other molecule in the functional coding or non-coding part of the target gene, a mutation or removal of the functional coding or non-coding part of the target gene, the usage of specific siRNAs, miRNAs or combinations thereof, or any other means known to a skilled person.

The term 'mutation' refers to a spontaneous mutation and/or to an induced mutation in the genome of said fungal strain. Said mutation can be a point mutation, deletion, insertion or any other type of mutation.

Similarly, a 'dysfunctional' polypeptide as defined above can be obtained by any (small) compound or other means to weaken or disrupt the function of the target genes of the present invention. Means to silence the transcription or translation or means to disrupt the function of the target genes of the present invention or means to disrupt the function of a necessary regulator/activator protein of the target genes comprise the usage of any molecule such as—but not limited to—an antibody, an amino acid, a peptide, a small molecule, an aptamer, a ribozyme, an oligoribonucleotide sequence such a dsRNA used to initiate RNA interference (RNAi) or an anti-sense nucleic acid. Such a molecule is thus capable to bind on a target protein or an activator/regulator protein thereof, or, is capable to interfere with the cellular synthesis of the target enzyme or of an activator/regulator thereof by—for example—binding and degrading mRNA's encoding for a target protein or an activator/regulator thereof.

A 'dysfunctional' CYP52M1 and FAO1 refers to an enzyme with reduced activity, obtained by any method known by the person skilled in the art. Non-limiting examples of said methods are the introduction of point mutations, the usage of truncated or mutated enzymes, the usage of inhibitors or antibodies, and any of the methods described above.

The term 'dysfunctional' thus also refers to the absence of the specific genes mentioned above (cyp52M1 and fao1) in the genome of the applied fungal strain.

The genes and their encoded enzymes CYP52M1 and FAO1 are well known in the art and are—for example—described in WO2011154523 (CYP52M1) and in Takahashi et al. (2016) (FAO1).

Hence, and more specifically the present invention relates to a method as described above wherein the gene encoding for the CYP52M1 cytochrome P450 monooxygenase and the gene encoding for the FAO1 fatty alcohol oxidase are knocked out.

The present invention further relates to a method as described above wherein said alcohol having an aliphatic tail chain length of at least 6 carbons is hexanol, octanol, decanol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, isostearyl alcohol, oleyl alcohol, nonadecyl alcohol, arachidyl alcohol or a mixture thereof.

The present invention also relates to a method as described above, wherein said fully symmetrical bola sophorosides are (tetra-, tri-, di- or mono-) acetylated.

With the term 'acetylated' is specifically meant bola- or alkyl sophorosides which contain an 'acetyl' functionality on position 6' or 6" of one or both of the two sophorose moieties present in said bola or alkyl sophorosides. The term 'acetylation' (or ethanoylation) more generally describes a reaction that introduces an acetyl functional group into a chemical compound resulting in an acetoxy group i.e. the substitution of an acetyl group for an active hydrogen atom. A reaction involving the replacement of the hydrogen atom of a hydroxyl group with an acetyl group ($CH_3$ CO) yields a specific ester, the acetate.

The present invention also relates to a mutated fungal strain such as a *Starmerella bombicola* strain having a dysfunctional CYP52M1 cytochrome P450 monooxygenase and a dysfunctional FAO1 fatty alcohol oxidase.

This latter strain can be made by any method known in the art and as is described above. A specific but non-limiting method to create a CYP52M1 cytochrome P450 monooxygenase and FAO1 knockout strain is described further in the 'materials and methods' section of the 'Examples' section.

Hence, and more specifically, the present invention relates to a mutated fungal strain such as a *Starmerella bombicola* strain as described above wherein said gene encoding for the CYP52M1 cytochrome P450 monooxygenase and said gene encoding for the FAO1 fatty alcohol oxidase are knocked out.

The present invention further relates to the usage of a mutated fungal strain such as a *Starmerella bombicola* strain as described above to produce fully symmetrical bola sophorosides which are free from contaminating fatty acid containing sophorolipids as is described above.

Figure 6:
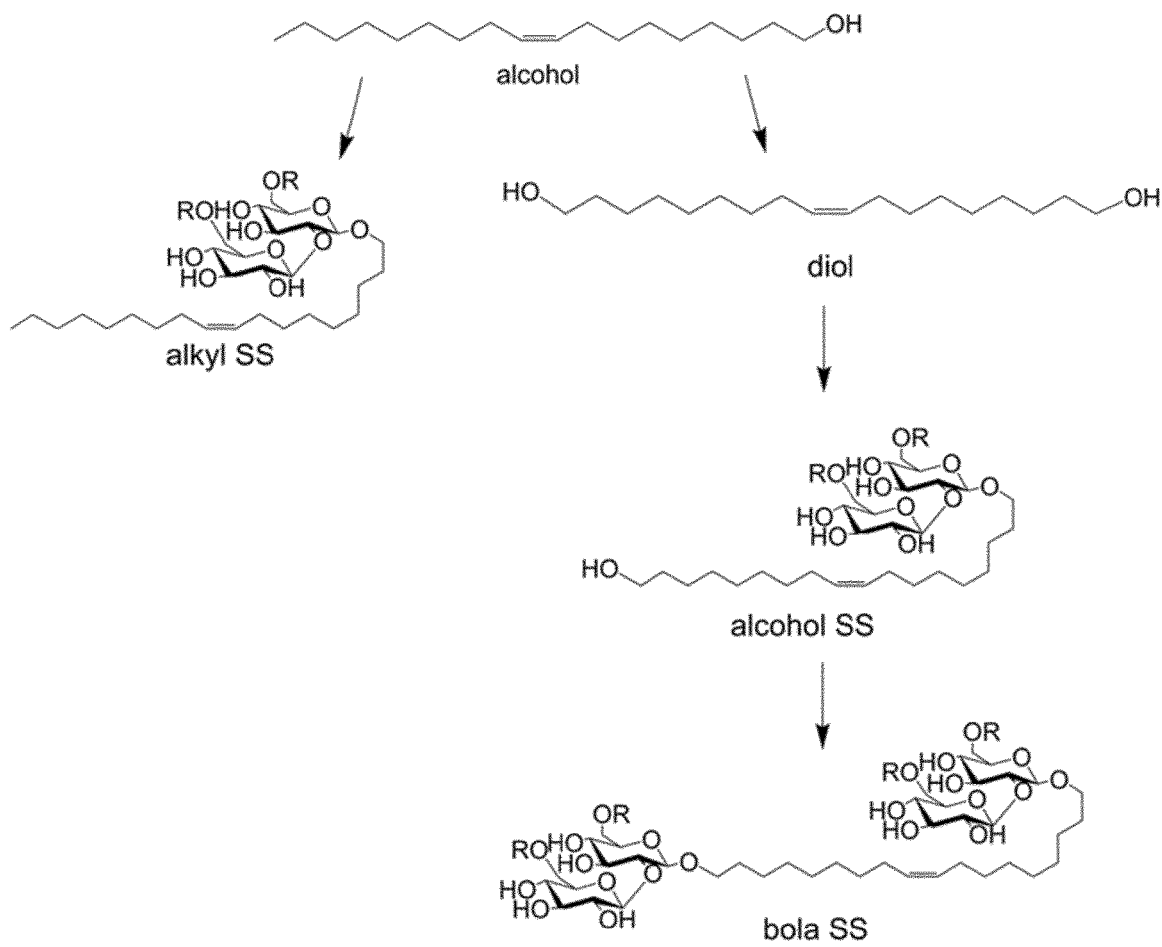
FIG. 6: Overview of the production pathway using the Δcyp52M1Δfao1 strain and feeding the latter with oleyl alcohol. By knocking out the cyp52M1 gene, it was expected that only glycosylation could be performed as suggested in route A, giving rise to an acetylated mixture of alkyl SS (up to two acetylations), acetylations are represented as R groups. However, due to another unknown and unexpected activity of presumably a CYP52 enzyme in S. bombicola, hydroxylation was observed, which gave rise to acetylated bola SSs (up to four acetylations) after glycosylation. In the end, a mixture of mainly bola SSs and minor alkyl SSs was found. Hydroxylation solely occurred terminally, in contrast to the ΔatΔsbleΔfao1 strain reported in Van Renterghem et al. (2018).

The present invention also relates to the usage of a mutated fungal stain such as a *Starmerella bombicola* strain as described above to produce fully symmetrical diols. The latter diols are the precursors of the symmetrical bola sophorosides as is shown in FIG. 6.

The present invention further relates to the usage of a mutated fungal strain such as a *Starmerella bombicola* strain as described above wherein said symmetrical bola sophorosides are part of a mixture further comprising alkyl sophorosides.

The latter mixtures are formed because some fatty alcohol molecules are glycosylated by subsequent action of the enzymes UGTA1 and UGTB1 (see also further) and then secreted before the fed fatty alcohol could be hydroxylated. This gives rise to alkyl sophoroside production as 'unfinished' bola sophorosides or other bola sophorosides intermediates together with the production of bola sophorosides.

Hence, the present invention also relates to the usage of a mutated fungal strain such as a *Starmerella bombicola* strain as described above to produce alkyl sophorosides.

Indeed, the latter alkyl sophorosides are produced when the fed fatty alcohol is not hydroxylated at the other side of the aliphatic chain and glycosylated and secreted as alkyl sophorosides.

The present invention further relates to a mutated fungal strain as described above, wherein said fungal strain further comprises a dysfunctional glucosyltransferase (UGTB1) that is responsible for the second glucosylation step in the sophorolipid/sophoroside biosynthetic pathway.

The term 'A glucosyltransferase that is responsible for the second glucosylation step in the sophorolipid biosynthetic pathway' is described in detail in WO2011154523. Indeed WO2011154523 discloses that there is a first glycosylation (see example 2 of WO2011154523) and a second glycosylation step (see example 3 of WO2011154523) in the sophorolipid pathway wherein a 'first' (i.e. UGTA1) and a 'second' glycosyltransferase (i.e. UGTB1 having Genbank Accession number HM440974 and as is also described in detail in Saerens et al. 2011 (Yeast: 279-292)), are involved.

The term 'dysfunctional' is described above.

The present invention also relates to the use of mutated fungal strain as described above to produce symmetrical bola glucosides.

The term 'symmetrical bola glucosides' relates to a glucoside with one glucose molecule at each side of the fatty hydrophobic linker or aliphatic tail (or chain) through two terminal (ω) glycosidic linkages as described above.

The present invention relates to both 'acetylated' and 'non-acetylated' symmetrical bola glucosides but specifically relates to the use of mutated fungal strain as described above wherein said symmetrical bola glucosides are acetylated.

The term 'acetylated' is described above.

EXAMPLES

Materials and Methods

Strains, Media and Culture Conditions

As parental strain, the SL deficient Δcyp52M1 strain *S. bombicola* was used (Van Bogaert et al., 2013a). A *S. bombicola* fatty alcohol oxidase fao1 knockout was obtained similarly as described by Van Renterghem (2018) by integrating the ura3 gene under the regulatory control of its own promotor and tyrosine kinase (tk) terminator at the respective fao1 loci in the Δcyp52M1 strain. Three transformant colonies of the new strain were evaluated in terms of growth and glycolipid production, in parallel with the Δcyp52M1 parental strain. Cultivation, selection and transformation were performed as described by Lodens et al. (2018).

Production experiments using *S. bombicola* were performed using the production medium described by Lang et al. (2000). For shake flask experiments, 5 ml tube cultures were set up 24 h (30° C.), before transferring to shake flasks (4% inoculation). Production experiments were executed with feeding of fatty alcohols: oleyl alcohol, stearyl alcohol, lauryl alcohol, myristyl alcohol or cetyl alcohol which were added after 48 h of cultivation. The Δcyp52M1Δfao1 strain was also assessed without addition of the hydrophobic alcohol. For every production experiment, cultivation was stopped when glucose was depleted from the medium. Experiments were performed in duplicate, and average values with standard deviations are presented.

Molecular Techniques
General Techniques

Figure 2:
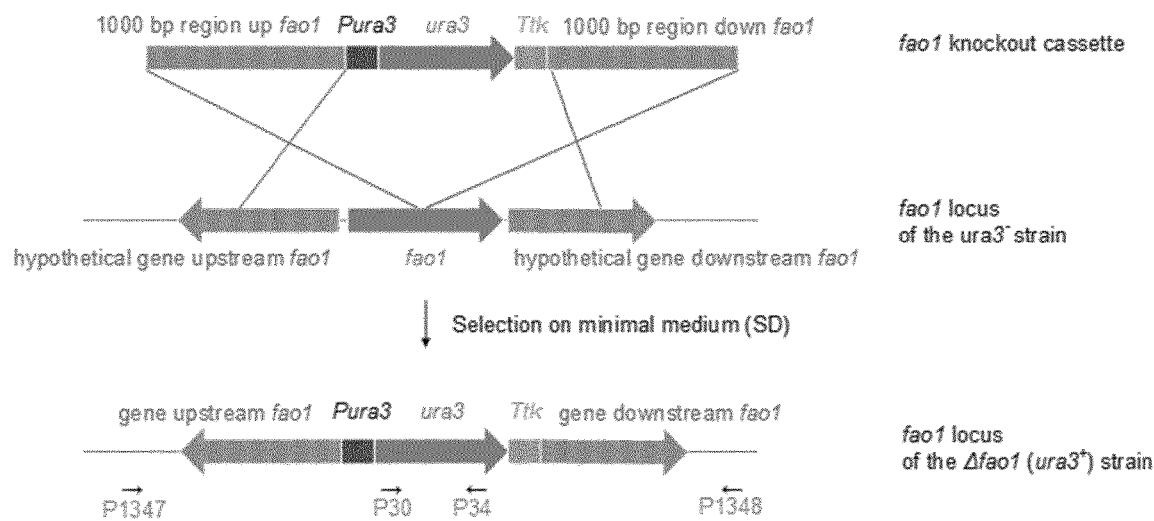
FIG. 2: Schematic representation of the fatty alcohol oxidase (fao1) knockout cassette and integration thereof at the fao1 locus of the ura3 auxotrophic Δcyp52M1 strain. The ura3 gene was used as marker gene. The respective primer pairs for colony PCR to check correct integration of the fao1 knockout cassette are depicted in orange.

General molecular techniques were employed as described by Green and Sambrook (2012). Linear deletion cassettes were generated from vector backbones cloned and maintained in *E. coli*, based on the pGEM-T (Promega) and pJET (Thermo Fisher) vectors and cloning steps are described below. All primer sequences are represented in Table 1 and a graphical representation of the strain construction is shown in FIG. 2.

TABLE 1

Primers used for the creation of knockout strain of the *S. bombicola* fatty alcohol oxidase gene (fao1) in the Δcyp52M1 strain.

| Primer names | '5-sequence-3' |
| --- | --- |
| P30_FOR_checkpromIN | AAGGCGGGCTGGAATGCATATCTGAG (SEQ ID NO 1) |
| P34_REV_checkcassIN | GATGTCGAATAGCCGGGCTGCTAC (SEQ ID NO 2) |
| P276_pJET_Rev | AAGAACATCGATTTTCCATGGCAG (SEQ ID NO 3) |
| P625_pJET_For | CGACTCACTATAGGGAGAGCGGC (SEQ ID NO 4) |
| P1001_FOR_FAO1_extgibpJET | CTCGAGTTTTTCAGCAAGATTGCCAAGTCGTTCAACACAG (SEQ ID NO 5) |
| P1002_REV_FAO1_extgibpJET | AGGAGATCTTCTAGAAAGATCTGAGACAGCAGCTTGTCAC (SEQ ID NO 6) |
| P1003_FOR_pJETextGib_FAO1 | GTGACAAGCTGCTGTCTCAGATCTTTCTAGAAGATCTCCTAC (SEQ ID NO 7) |
| P1004_REV_pJETextGib_FAO1 | CTGTGTTGAACGACTTGGCAATCTTGCTGAAAAACTCGAGCCATC (SEQ ID NO 8) |
| P1020_FOR_FAO1 | TGCCAAGTCGTTCAACACAG (SEQ ID NO 9) |
| P1021_REV_FAO1 | CTGAGACAGCAGCTTGTCAC (SEQ ID NO 10) |
| P1022_REV_checkFAO1KO | GCCTTGGCATTCAACATCTCAGGGAATC (SEQ ID NO 11) |
| P1023_FOR_checkFAO1KO | GCACGCCCTTAGCTTCAGAG (SEQ ID NO 12) |
| P1062_FOR_Pura3_extgib_upFAO1 | GACTGAGATGACGGAAGAGGCCCGAACATACCAGTTTCGC (SEQ ID NO 13) |
| P1063_REV_tTK_extgib_downFAO1 | AAGCTTAGTGAGATCCGCGTGAACAAACGACCCAACACCC (SEQ ID NO 14) |
| P1064_FOR_downFAO1_extgibtTK | GGGTGTTGGGTCGTTTGTTCACGCGGATCTCACTAAGCTTC (SEQ ID NO 15) |
| P1065_REV_upFAO1_extgibPura3 | GCGAAACTGGTATGTTCGGGCCTCTTCCGTCATCTCAGTC (SEQ ID NO 16) |
| P1347_FOR_FAO1_up_check | GCCAGTGCAACAAGTATGAG (SEQ ID NO 17) |
| P1348_REV_FAO1_down_check | GACCAGGCTAAACGCATCAC (SEQ ID NO 18) |

Creation of the Δcyp52M1Δfao1 Knockout Strain

The creation of the fao1 knockout cassette is described Van Renterghem et al. (2018) and was used to transform the S. bombicola Δura3::0Δcyp52M1::Pgapd_hph_Ttk strain, or further on called the Δura3Δcyp52M1 strain. The hph gene was isolated from *Streptomyces hygroscopus*, and encodes for hygromycin B phosphotransferase resistance (Gritz & Davies, 1983). After transformation, the ura3 positive colonies were selected on selective SD medium. Correct integration of the cassette was confirmed by colony PCR. For the newly-created Δura3::0Δcyp52M1::Pgapd_hph_tTK Δfao1::Pura3_ura3_Ttk strain, further on called Δcyp52M1Δfao1, respectively, three successful colonies were chosen.

Downstream Processing and Characterization

The purification of the generated products of the Δcyp52M1Δfao1 strain when fed with oleyl was done by performing alkaline hydrolysis (pH 12, 5 M NaOH, 37° C., 1 h) to fully deacetylate the glycolipids to obtain a more uniform product. The purified and dried product was further fractionated by preparative liquid chromatography (PLC) for NMR analysis (see below).

Preparative Layer Chromatography (PLC)

Uniplate 20×20 cm PLC plates coated with 2 mm silica gel, impregnated with a green fluorescent indicator (F254) (Analtech) were used. First, 100 mg of sample was dissolved in MilliQ water. Subsequently, the solution was applied as a long streak at 2 cm from the bottom of the plate. The PLC plate was put in a solvent chamber containing the SL solvent mixture chloroform/methanol/water (65/15/2, v/v/v) (Asmer et al., 1988). After solvent development and respective evaporation, the plate was put under UV light at 254 nm. Subsequently, the highlighted zone of interest was scraped off using a scalpel and the scraped-off silica gel was collected. The compound was subsequently resolved by adding 20 mL MilliQ water to the falcon and centrifuged for 10 minutes at 4500 rpm. The supernatant was collected, and the process was repeated. The total supernatant, containing the bola SS product, was filtered (cut-off 0.22 μm, Millex® GV) to remove residual silica gel particles. Finally, the water was removed by using an Alpha 1-4 lyophilisator (Christ) to obtain a dry and highly-pure product, suitable for NMR analysis.

Analytical Techniques

Follow-Up of Growth

Optical density (OD) of cultures was measured at 600 nm using the Jasco V 630 Bio spectrophotometer (Jasco Europe) of 1 mL samples diluted with physiological solution (9 g/L NaCl). The viability of yeast cells in cultivation experiments was assessed by determining colony forming units (CFUs) which were expressed as the average logarithm of CFUs per culture volume as log (CFU/mL) (Saerens et al., 2011). Alternatively, Cell Dry Weight (CDW) was determined by centrifuging 1 mL fermentation samples at 14000 rpm for 5 min in tared Eppendorf tubes, and subsequently washing the cell pellets twice with 1 mL physiological solution. The remaining cell pellet was put into a 70° C. oven for 5 days and then weighed afterwards. The CDW (g/L) was calculated after subtraction of the empty weight of the Eppendorf tube.

Follow-Up of Glucose Concentration

Glucose concentrations were determined using the 2700 Select Biochemistry Analyser (YSI Inc.) or using Ultra Performance Liquid Chromatography (Waters Acquity H-Class UPLC), coupled with an Evaporative Light Scattering Detector (Waters Acquity ELSD Detector) (UPLC-ELSD). For the UPLC analysis, an Acquity UPLC BEH Amide column (130 Å, 1.7 μm, 2.1×100 mm) (Waters) was used at 35° C. and an isocratic flow rate of 0.5 mL/min of 75% acetonitrile and 0.2% triethylamine (TEA) was applied (5 min/sample). For the ELS detection, the nebulizer was cooled to 15° C. and the drift tube was kept at a temperature of 50° C. The linear range was found to lie between 0 and 5 g/L glucose, using a gain of 100 for ELS detection (Empower software). To express glucose consumption, a linear curve was fitted through the obtained glucose concentrations by UPLC-ELSD, and the respective slope was taken and denoted as the glucose consumption rate (g/L·h).

Analysis of Glycolipids

Samples for glycolipid analysis were prepared by shaking a mixture of 1 mL of pure ethanol and 0.5 mL of fermentation broth vigorously for 5 minutes. Subsequently, after centrifugation for 5 minutes at 15000 rpm, the cell pellet was removed and the supernatant was filtered using a PTFE filter (cut-off 0.22 μm, Novolab) and adequately diluted in 50% ethanol (unless stated otherwise) before analyzing on (Ultra) High Pressure Liquid Chromatography-Mass Spectrometry ((U) HPLC-MS) and (U) HPLC-ELSD (Evaporative Light Scattering Detector).

HPLC-MS was performed using an LC (Shimadzu), coupled to an MS (Micromass Quattro LC) detection system. The different components were separated by polarity on a Chromolith Performance RP-18 Endcapped 100-4.6 mm column (Merck KGaA) at 30° C. The LC-MS method uses a gradient elution based on two solvents: MilliQ with 0.5% acetic acid, and pure acetonitrile (ACN). During the analysis, a flow rate of 1 mL/min was applied. The gradient starts with 5% acetonitrile and increases linearly until 95% over the course of 40 min. After this, the 95% acetonitrile is held for another 10 min, after which this is brought back to 5% acetonitrile in 5 min. The total analysis time per sample is 60 min/sample. The scanning range of the MS was set to 215-1100 g/mol. Using similar conditions as mentioned for HPLC-MS, HPLC-ELSD analysis was performed by Varian Prostar HPLC (ThermoScientific), coupled with an 2000ES ELSD (Alltech) at 40° C. All other conditions are similar as mentioned for the HPLC-MS.

UPLC-ELSD analysis was performed on a Acquity H-Class UPLC (Waters) and Acquity ELSD Detector (Waters), employing the same column and analysis method as UPLC-MS. For the ELSD detection, the nebulizer was cooled at 12° C. and the drift tube was kept at a temperature of 50° C., the gain was set to 200. To quantify the glycolipids, a dilution series of purified product was prepared. An available C18:1 acetylated bola SS purified batch (batch number SL24A) and purified acetylated C16:0 alkyl SS batch (batch number aAlkC16_2) were employed for quantification of bola and alkyl SS, respectively.

Alternatively, UPLC-MS was performed with an Accela (ThermoFisher Scientific) and Exactive Plus Orbitrap Mass Spectrometer (ThermoFisher Scientific). For glycolipid analysis, an Acquity UPLC CSH C18 column (130 Å, 1.7 μm, 2.1 mm×50 mm) (Waters) and a gradient elution system based on 0.5% acetic acid in milliQ (A) and 100% acetonitrile (B) at a flow rate of 0.6 mL/min was applied. The method was as follows: the initial concentration of 5% B (95% A) increases linearly until 95% B (5% A) during the first 6.8 min, and then linearly decreases again to 5% B (95% A) during 1.8 min. Subsequently, 5% B (95% A) is maintained until the end of the run (10 min/sample). Negative ion mode was used, and 2 μL samples were injected. MS detection occurred with a Heated Electrospray Ionization (HESI) source and conditions were set to detect masses ranging from 215-1300 m/z in a qualitative way.

All $^1$H and $^{13}$C NMR spectra were recorded at 400 and 100.6 MHz, respectively, on a Bruker Avance III, equipped with $^1$H/BB z-gradient probe (BBO, 5 mm). DMSO-[D6] was used as solvent, and as internal chemical shift standard (2.50 ppm for $^1$H and 39.52 ppm for $^{13}$C). All spectra were processed using TOPSPIN 3.2 software. Attached Proton Test (APT), $^{13}$C, COSY, and HSQC spectra were acquired through the standard sequences available in the Bruker pulse program library. Custom settings were used for HMBC (32 scans), TOCSY (100 millisec MLEV spinlock, 0.1 sec mixing time, 1.27 sec relaxation delay, 16 scans), and H2BC (21.8 millisec mixing time, 1.5 sec relaxation delay, 16 scans), according to literature (Gheysen, Mihai, Conrath, & Martins, 2008; Petersen et al., 2006).

Statistical Analysis

When two different groups were compared, the Welch's test was performed with a 95% confidence level using GraphPad Prism 7.04 software. For multiple group comparisons, analysis of variance (ANOVA) with Bonferroni's multiple comparison test correction with a 95% confidence level using GraphPad Prism 7.04 software was employed. For parameters pH, CFU, OD and glucose consumption, average values were taken when the yeast cells attained their stationary phase (after 48 h of cultivation). In general, data represented in graphs are the average and standard deviation of two experimental replicates (unless stated otherwise).

Results

Construction of Knockout Strains

The fatty alcohol oxidase fao1 knockout cassette (described in Van Renterghem et al., 2018) was used to transform the S. bombicola Δcyp52M1Δura3 strain. After selection of the ura3+ colonies on selective SD plates, correct integration at both sides of the knockout cassette was controlled by performing colony PCR using two primer combinations (see Table 1). Three correct colonies of the newly created Δcyp52M1Δfao1 strain were selected for further characterization. The three selected transformants of the novel strain behaved similar to each other in terms of OD, CFUs, glucose consumption and glycolipid production. Therefore, only one colony is discussed in the next section for comparison with the parental Δcyp52M1 strain in terms of growth, pH, glucose consumption and glycolipid production.

Initial Characterization of Knockout Strain

For the wild type S. bombicola, colza oil (60-80% oleic acid) or pure oleic acid results in the best SL titers (Asmer et al., 1988; Rau et al., 2001) i.e. a hydrophobic substrate with C18 carbon chain length. Therefore, the newly created fao1 knockout strain was first assessed on shake flasks fed with a C18 fatty alcohol, i.e. oleyl alcohol (C18:1) as hydrophobic substrate.

Growth, pH and Glucose Consumption

Figure 3:
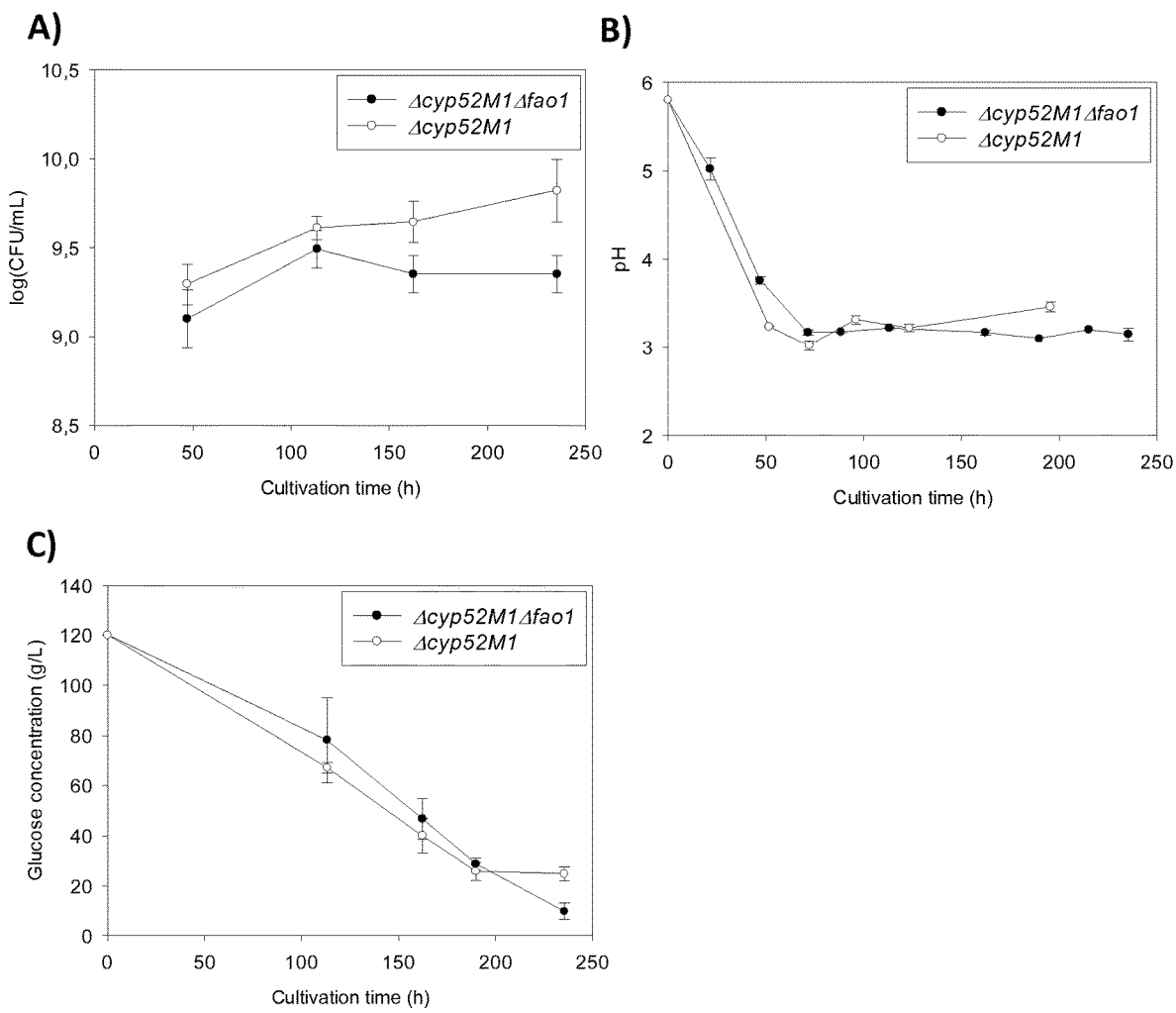
FIG. 3: Important parameters for characterization of the Δcyp52M1Δfao1 strain (●), compared to the parental Δcyp52M1 strain (○) in shake flask. The average values and respective standard deviations are presented of A) log (CFU/mL) s, B) pH and C) glucose concentration (g/L). 1.8 (w/v) % of oleyl alcohol was added after 48 h of cultivation as hydrophobic substrate.

Important parameters such as log (CFU/mL), pH and glucose consumption are depicted in FIG. 3. Average values and standard deviations of assessed duplicates are presented. $OD_{600}$ evolution was not presented, due to interferences of the measurements with the oleyl alcohol substrate. In terms of log (CFU/mL) values in function of cultivation time (FIG. 3A), no significantly different CFU values were obtained between the new strain and reference strain. The observed pH drop was equal (FIG. 3B). The glucose consumption rate for the Δcyp52M1Δfao1 and parental strain are similar (0.47±0.06 and 0.47±0.01 g/L·h), as presented in FIG. 3C.

Glycolipid Production

Figure 4:
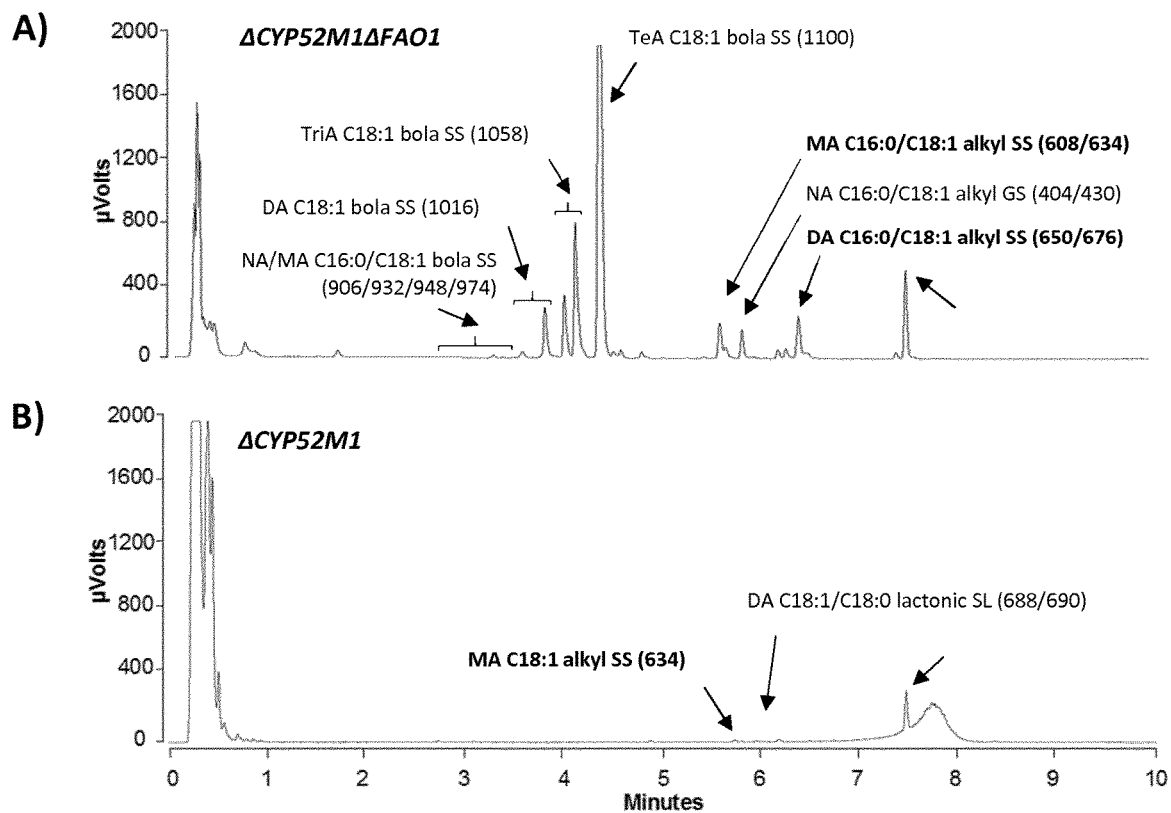
FIG. 4: UPLC-ELSD chromatograms of end samples of shake flask experiments for the A) Δcyp52M1Δfao1 strain, compared to the B) Δcyp52M1 strain both fed with 1.8 (w/v) % oleyl alcohol (both 3× diluted). Respective masses determined with UPLC-MS are depicted above the respective peaks. In bold, masses corresponding to alkyl SS are depicted. An overview of possible glycolipid masses is given in Table 2.

When looking at glycolipid production of the assessed strain, depicted in FIG. 4, distinctly different production profiles for the Δcyp52M1Δfao1 strain can be observed compared to the Δcyp52M1 parental strain.

The parental Δcyp52M1 strain (FIG. 4B) produced none (or very minor) amounts of glycolipids (<7 min). A small peak corresponding to oleic acid (282 g/mol) is visible at later retention times (>7 min) (similarly as the one observed for the Δcyp52M1Δfao1 strain). The fact that almost no alkyl SS are detected, indicates that the fed oleyl alcohol is mainly oxidized to the corresponding oleic acid by the still functional w-oxidation pathway (as FAO is not knocked out). Subsequently, as hydroxylation of oleic acid is inhibited by the cyp52M1 knockout, the glucosyltransferases cannot glycosylate the fatty acid, so the oleic acid accumulates or is broken down by the β-oxidation.

Figure 5:
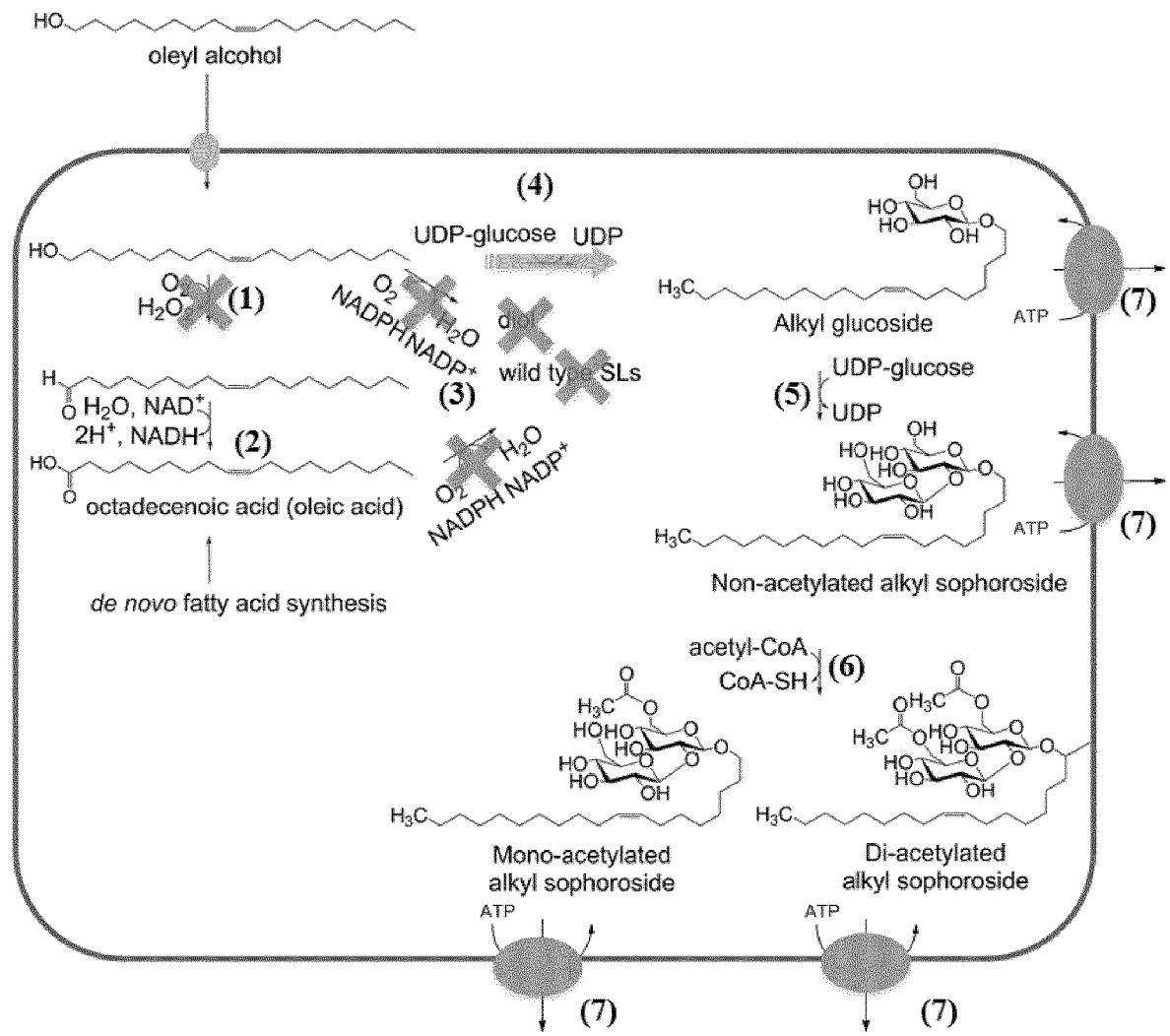
FIG. 5: Proposed production pathway of alkyl sophorosides (SSs) in the Δcyp52M1Δfao1 strain when fed with oleyl alcohol. (1) Fatty alcohol oxidase fao1, (2) fatty aldehyde dehydrogenase FAD, (3) cytochrome P450 monooxygenase CYP52M1, (4) glucosyltransferase UGTA1, (5) glucosyltransferase UGTB1, (6) acetyltransferase AT and (7) SL transporter MDR. By knocking out the fao1 and cyp52M1 gene (indicated by crosses), the fatty alcohol is not converted towards the corresponding fatty aldehyde, nor to the corresponding diol (in this case 1,18-octadecenediol) nor are de novo fatty acids hydroxylated (indicated by cross) to then enter the SL biosynthesis. In this way, the accumulating alcohol is directly glucosylated by glucosyltransferases UGTA1 and UGTB1, which sequentially add glucose molecules on the fatty alcohol and alkyl glucoside backbone respectively. A non-acetylated alkyl SS is obtained, which should be acetylated by the acetyltransferase AT, giving rise to a mixture of non-, mono- and di-acetylated alkyl SSs. Finally, these glycolipids are likely to be transported out of the cell, presumably by the MDR transporter responsible for secretion of wild type SLs (Van Bogaert et al., 2013).

In contrast to the parental strain, for the Δcyp52M1Δfao1 strain (FIG. 4A) glycolipid production is clearly observed. Significant amounts of glycolipids were found at retention times between 3.0-4.5 min and minor amounts between 5.5-6.5 min. After UPLC-MS analysis, surprisingly it was found that the masses in the early retention range (3-4.5 min) actually corresponded to bola SSs (900-1100 g/mol range), instead of the aimed for alkyl SS (550-700 g/mol range). Alkyl SS were indeed detected, but only in the abovementioned minor amounts between 5.5-6.5 min. This synthesis of bola SSs is theoretically (based on the art) impossible in this strain, as diol formation (see FIG. 5) (necessary for bola SS synthesis) through hydroxylation of the fed fatty alcohol should not be possible due to the deletion of the cyp52M1 gene. Indeed, no such action is observed in the parental strain (see FIG. 4B), which as mentioned in the art indeed does not show any oxidation/hydroxylation activity towards oleyl alcohol (see FIG. 4B) nor on oleic acid and/or rapeseed oil (Van Bogaert et al., 2013).

Thus, surprisingly, the Δcyp52M1Δfao1 strain mainly produces bola SSs when fed with oleyl alcohol (FIG. 6), corresponding to the early retention times (3.0-4.5 min). As the AT gene is not knocked out in this strain (in contrast to the strain designed to produce bola SSs (Soetaert et al., 2013; Van Renterghem et al., 2018), acetylation of the bola SSs is also observed for this new strain described above. The tetra-acetylated C18:1 bola SS (1100 g/mol) at 4.4 min is the most abundant component of the bola SSs, followed by the less abundant tri- and di-acetylated ones (1016 and 1058 g/mol, respectively). Non- and mono-acetylated C18:1 bola SS were also detected (respective 932 and 974 g/mol). The fact that the mono-, di- and tri-acetylated bola SS appear in two different peaks at 4.05 and 4.15 min, is probably explained by a different acetylation pattern of the molecule, similarly as shown for acidic SLs shown in literature (Davila et al., 1993; Saerens et al., 2011; Saerens, 2012). Besides C18:1 bola SSs, also C16:0 based SSs (906 g/mol) are detected arising from the C16 amounts in the fed oleyl alcohol substrate (contaminating amounts of 2-10% cetyl alcohol or 1-hexadecanol are present in the substrate). Minor amounts of alkyl SSs were also produced and mainly C18:1 non-, mono- and di-acetylated alkyl SSs were detected (592/634/676 g/mol, respectively), but also traces of C16:0 alkyl SSs were found (566/608/650 g/mol, respectively).

It thus appears that the fed alcohol is favorably hydroxylated to the corresponding diol, and as such goes through the glycosylation cycle of UGTA1 and UGTB1 twice, to give rise to bola SSs (see FIG. 6), instead of just accumulating into alkyl SSs. As the parental strain fed with alcohols did not produce these compounds when fed on oleyl alcohol, it appears that the combination of the cyp52M1 and fao1 knockout is crucial.

To enable detailed characterization of the produced compounds, the bola SSs and alkyl SSs were purified from the mixture as described.

NMR Structure Analysis

NMR analysis was performed on a purified non-acetylated C18:1 bola SSs standard derived from the broth of the Δcyp52M1Δfao1 strain.

Figure 7:
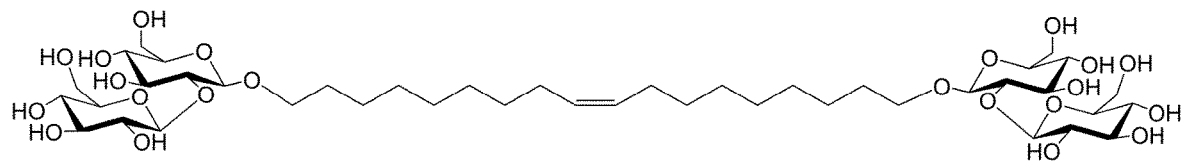
FIG. 7: Structural confirmed composition of the purified oleyl alcohol-based (C18:1) bola SS produced by the Δcyp52M1Δfao1 strain. Only 100% terminal (w) hydroxylated compounds were found.

Surprisingly, NMR analysis showed that in the produced bola SSs, both sophorose moieties exclusively linked in a terminal (w) fashion to the hydrophobic linker, presented in FIG. 7. A full symmetrical glycolipid molecule is thus obtained, with chemical formula C42H76O22.

Feeding Different Chain Lengths of Fatty Alcohols

Unexpectedly, no successful uniform production of either bola SSs or alkyl SSs was obtained for the Δcyp52M1Δfao1 strain when feeding with oleyl alcohol. Instead, mixtures of both were found, although the majority of the novel glycolipids were (acetylated) bola SSs and only minor amounts of alkyl SS were produced. The production of tetra-acetylated bola SS was unexpected, since the CYP52M1 enzyme was thought to be the only enzyme involved in glycolipid production thus far in S. bombicola. To assess the influence on the chain lengths of primary alcohols to the glycolipid production, different substrates were fed to the Δcyp52M1Δfao1 strain. The parental strain Δcyp52M1 was assessed in parallel. Medium and long-chain alcohols were selected between a chain length of 12 and 18, similarly as reported by Davila et al. (1994) for alkanes. Similarly as for the experiments described above, the hydrophobic substrate was added after 48 h of cultivation.

Growth, pH and Glucose Consumption

Figure 8:
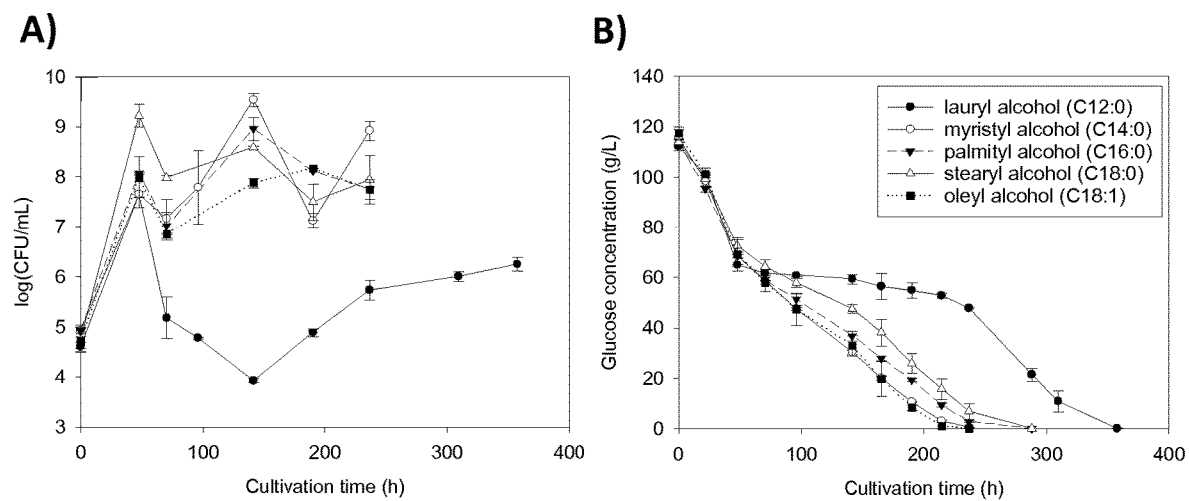
FIG. 8: A) log (CFU/mL) and B) glucose concentration of the Δcyp52M1Δfao1 strain in function of cultivation time when different primary alcohols were fed (lauryl, myristyl, palmityl, stearyl or oleyl alcohol). The average values and respective standard deviations are presented. The respective 1.8 (w/v) % of alcohol was added after 48 h of cultivation.

The addition of lauryl alcohol, myristyl alcohol, cetyl alcohol or oleyl alcohol did not significantly influence the CFU values for the Δcyp52M1 strain compared to the Δcyp52M1Δfao1 strain (FIG. 8).

However, a significant drop in CFUs was noticeable when lauryl alcohol was added, in contrast to all other fed substrates (FIG. 8A). Significant higher glucose consumption rates were found when myristyl or oleyl alcohol were fed compared to cetyl or stearyl alcohol (0.48 g/L·h vs 0.38 g/L·h). After addition of lauryl alcohol (48 h after inoculation), glucose consumption stopped. Only for the Δcyp52M1Δfao1 strain, the glucose consumption initiated again (0.33 g/L·h) 100 h after substrate addition, until all glucose was depleted. This is in line with the CFUs evolution (FIG. 8A).

The Δcyp52M1Δfao1 strain was also studied when no hydrophobic substrate was added. The CFUs and glucose consumption were not significantly different from the cultures fed with alcohols (except lauryl alcohol).

Glycolipid Production

Before addition of the primary alcohol, none of the Δcyp52M1Δfao1 and Δcyp52M1 cultures showed quantifiable glycolipid production. This was expected, as de novo fatty acids cannot be implemented into the glycolipid production pathway due to the cyp52M1 knockout, and the alcohol has to be fed in order to initiate novel glycolipid production.

Figure 9:
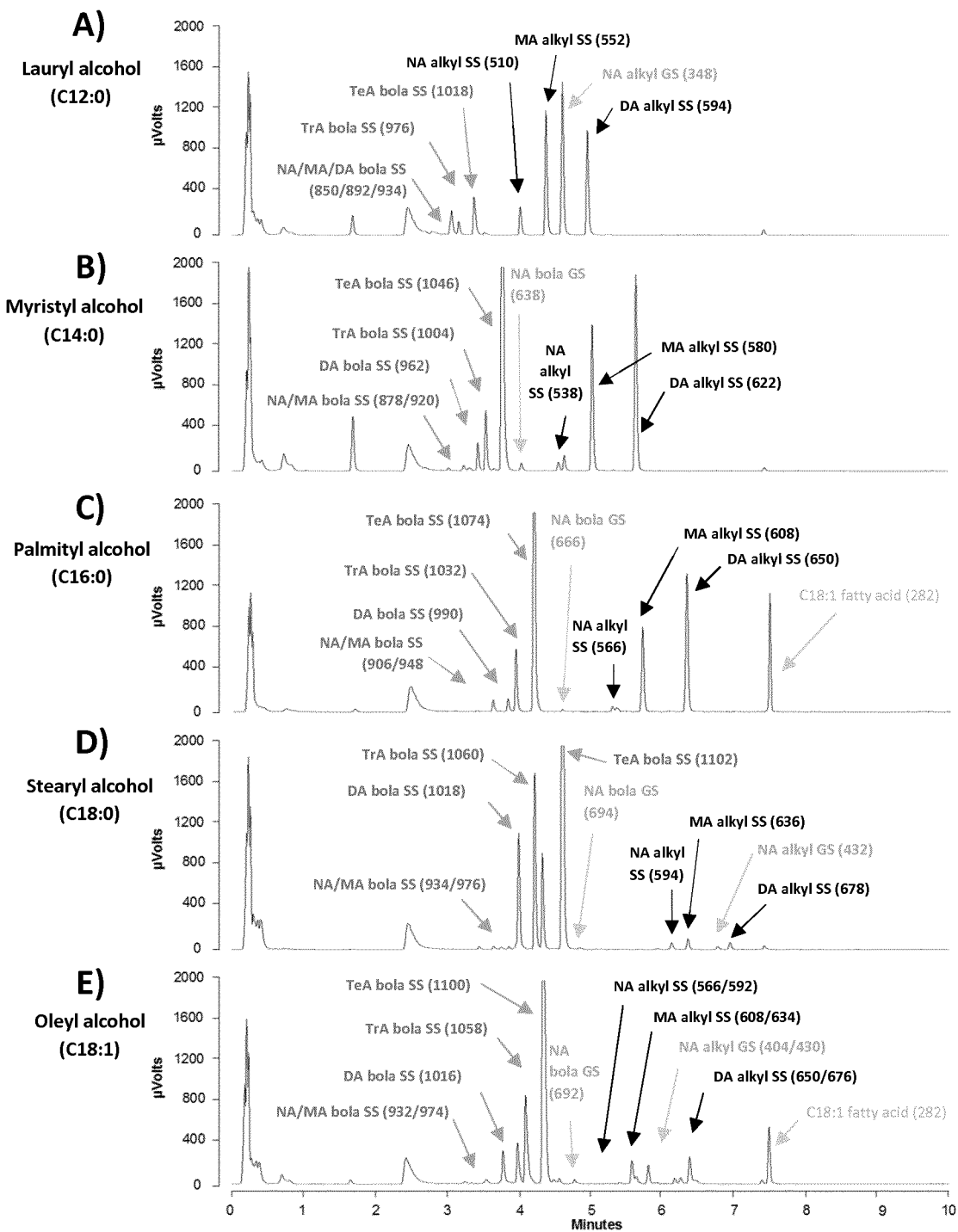
FIG. 9: End UPLC-ELSD chromatograms for the Δcyp52M1Δfao1 strain, fed with 1.8 (w/v) % (A) lauryl alcohol, (B) myristyl alcohol, (C) palmityl alcohol, (D) stearyl alcohol or (E) oleyl alcohol after 48 h of cultivation. All the end broths are 3× diluted. Retention times are indicated for the alkyl (up to two possible acetylations) and bola SSs (up to four possible acetylations). In bold, the glycolipid compounds are depicted when the respective fed alcohol was incorporated in bola SS (dark grey) and alkyl SS (black), alcohol and alkyl GS (light grey). The peaks with retention time <1 min correspond to a mixture of strong hydrophilic compounds present in the samples as sugars, proteins and salts.
Figure 10:
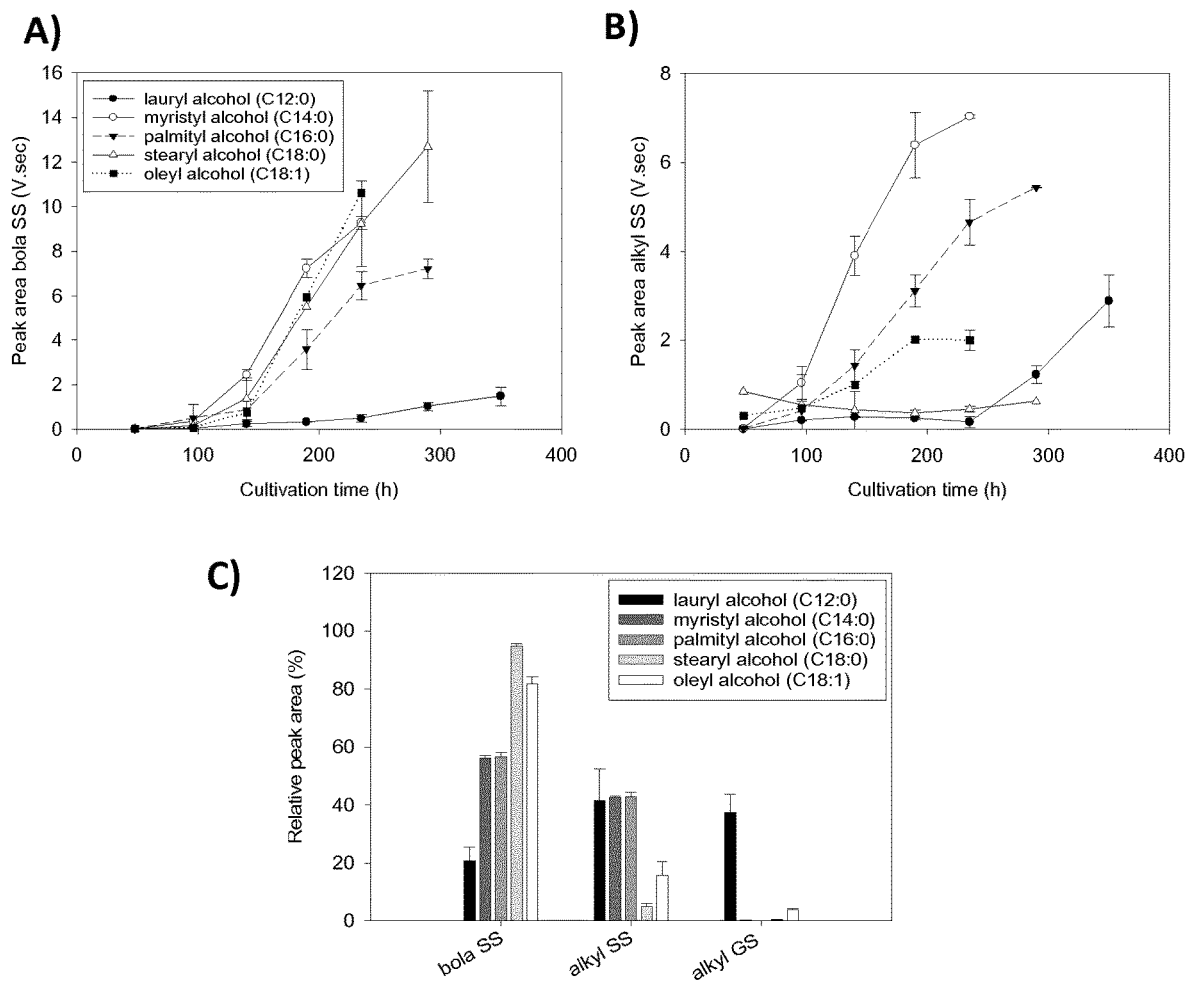
FIG. 10: Bola SS (A) and alkyl SS production (B) of the Δcyp52M1Afao1 strain in function of cultivation time, when fed with 1.8 (w/v) % of the respective primary alcohol after 48 h of cultivation. Production is expressed as the sum of peak areas (V·sec) determined by UPLC-ELSD. (C) Relative peak areas (%) of the end broths of the S. bombicola Δcyp52M1Δfao1 strain determined with UPLC-ELSD of the different glycolipid types, fed with 1.8 (w/v) % of lauryl alcohol (black), myristyl alcohol (dark grey), palmityl alcohol (medium grey), stearyl alcohol (light grey) or oleyl alcohol (white) after 48 h of cultivation.

After addition of the hydrophobic substrate for the Δcyp52M1 strain no peaks were visible after analysis on ELSD, which is in line with the expectations and with wat has been described before (Van Bogaert, 2010). Glycolipid end production profiles of the Δcyp52M1Δfao1 strain for the different fed primary alcohols analyzed on UPLC-ELSD are represented in FIG. 9. For each alcohol that was fed, a mixture of acetylated bola and alkyl SSs was produced. As expected, all produced glycolipids were originating from the fed alcohol directly. The latter is due to the fact that the cyp52M1 gene is knocked out, hence eliminating implementation of any de novo (mainly C16-C18) or generated (possible oxidation of the alcohol) fatty acids.

For lauryl alcohol, from non-up to tetra-acetylated C12:0 bola SS could be detected (580/934/976/1018 g/mol). Besides C12:0 bola SS, also non- to di-acetylated C12:0 alkyl SS (510/552/594 g/mol) were found at later retention times. However, the most abundant peak in the chromatogram corresponded to C12:0 alkyl glucosides (GS) (348 g/mol) which situated in between the mono- and di-acetylated alkyl SS peaks.

For myristyl and cetyl alcohol, very similar production profiles were observed. Clear retention times corresponding to C14:0 or C16:0 bola SSs (3.00-4.00 min and 3.00-4.3 min) and C14:0 or C16:0 alkyl SSs (4.5-5.8 min and 5.2-6.5 min) could be distinguished with respective acetylations. C14:0 and C16:0 non-acetylated alkyl GS (376 and 404 g/mol) were detected using MS,. Minor quantities of di-acetylated C14:0/or C16:0 alcohol SS (or bola GL) (638 or 666 g/mol) were detectable.

When the Δcyp52M1Δfao1 strain is fed with stearyl alcohol, again mixed production of acetylated C18:0 bola SSs (934/976/1018/1060/1102 g/mol) and C18:0 alkyl SS (594/636/678 g/mol) is observed. Additionally, minor amounts of C18:0 alkyl GS (432 g/mol) were detected. Similarly as for myristyl and cetyl alcohol, di-acetylated C18:0 alcohol SSs (or bola GL) (694 g/mol) were detected.

Addition of oleyl alcohol resulted in the glycolipid production profile described above. Also non-, mono- and di-acetylated C16:0 and C18:1 alkyl SS (566/608/650 g/mol and 592/634/676 g/mol respectively) and non-acetylated C16:0 and C18:1 alkyl GS (404 and 430 g/mol) were detected. Similarly as for the other alcohols, di-acetylated C18:1 alcohol SS (or bola GL) (692 g/mol) was also detected.

Generating the triple knock out strain (ΔCYP52M1 ΔFAO1 ΔUGTB1) for the production of symmetrical bola glucosides.

Figure 11:
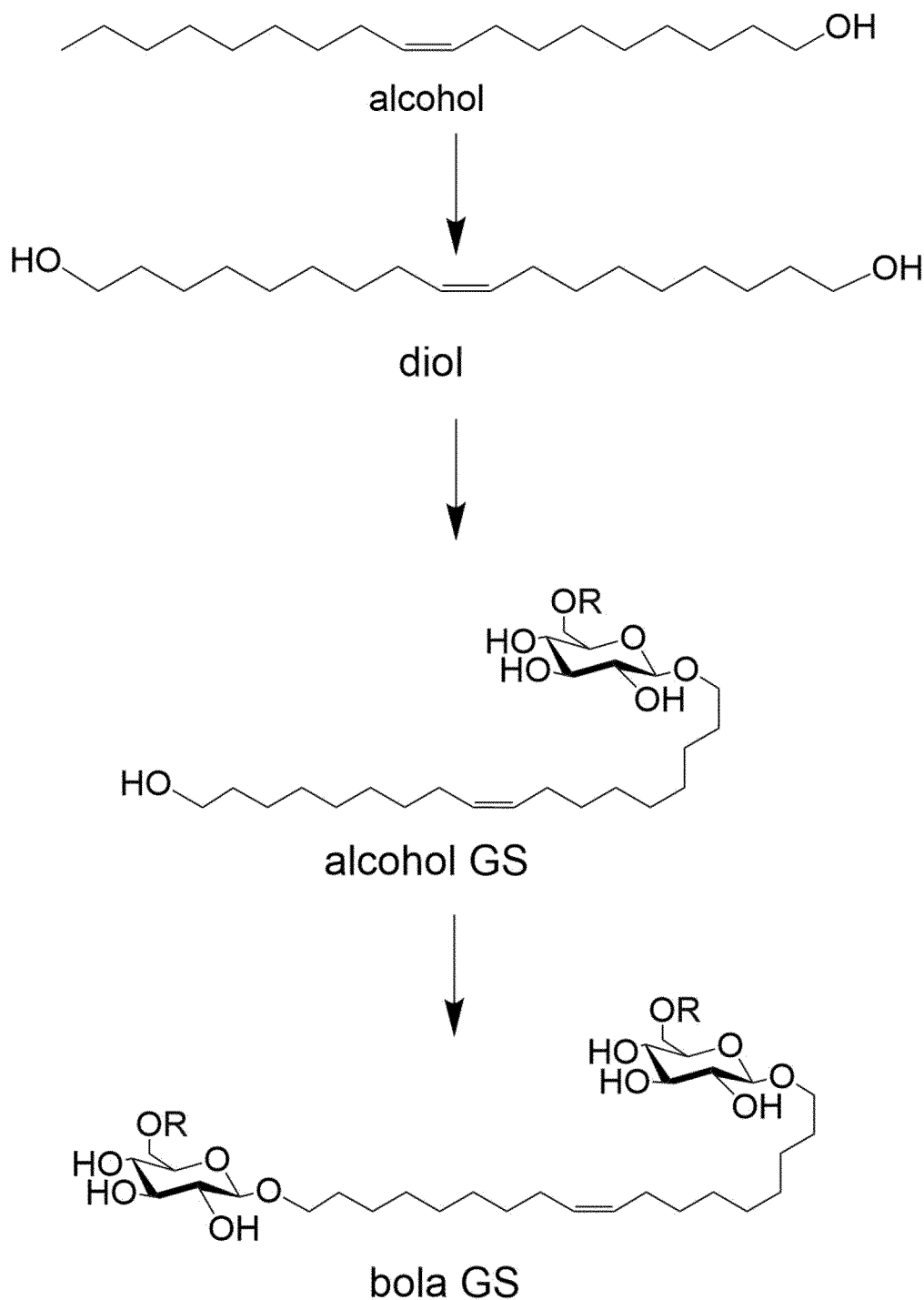
FIG. 11: The triple knock out strain (ΔCYP52M1 ΔFAO1 ΔUGTB1) produces (acetylated) symmetrical bola glucosides (GS). The figure shows the pathway to synthesize (acetylated) symmetrical bola glucosides. The bottom figure shows the actual (Acetylated) symmetrical bola glucosides C18:1. R═COCH3 or H.

For the generation of the triple knock out strain (ΔCYP52M1 ΔFAO1 ΔUGTB1), the ura3 marker was first removed from the double knock out strain (ΔCYP52M1 ΔFAO1) as described by Lodens et al., 2019 (Biotechnology and Bioengineering: 1-13). A linear UGTB1 knock-out cassette with ura3 marker was generated from plasmid "pGKO ugtB1" described by Saerens et al, 2011 using PfuUltra High Fidelity PCR (Stratagene) and the primerpair GTII-472F and GTII+239R: 5'-(GTII-472 For GAGAGTGGGACCTGATTC-3' (SEQ ID N° 19)/GTII+ 239Rev: 5'-CTGCTCTCAACACCGAGTGTAG-3' (SEQ ID N° 20)). This deletion cassette was transformed into the ura3 negative ΔCYP52M1 ΔFAO1 strain and correct transformants were selected. The resulting strain produces (acetylated) symmetrical bola glucosides as shown in FIG. 11.

REFERENCES

Asmer, H. -J. J., Lang, S. S., Wagner, F., & Wray, V. (1988). Microbial production, structure elucidation and bioconversion of sophorose lipids. *American Oil Chemists' Society*, 65 (9), 1460-1466.

Davila, A. -M. M., Marchal, R., & Vandecasteele, J. -P. P. (1994). Sophorose lipid production from lipidic precursors: Predictive evaluation of industrial substrates. *Journal of Industrial Microbiology*, 13 (4), 249-257. https://doi.org/10.1007/BF01569757

Davila, A. M., Marchal, R., Monin, N., & Vandecasteele, J. P. (1993). Identification and determination of individual sophorolipids in fermentation products by gradient elution high-performance liquid chromatography with evaporative light-scattering detection. *Journal of Chromatography A*, 648 (1), 139-149. https://doi.org/10.1016/0021-9673 (93) 83295-4

Gheysen, K., Mihai, C., Conrath, K., & Martins, J. C. (2008). Rapid identification of common hexapyranose monosaccharide units by a simple TOCSY matching approach. *Chemistry-A European Journal*, 14 (29), 8869-8878. https://doi.org/10.1002/chem. 200801081

Green, M. R., & Sambrook, J. (2012). *Molecular Cloning: A laboratory manual*. Fourth Edition.

Gritz, L., & Davies, J. (1983). Plasmid-encoded hygromycin B resistance: the sequence of hygromycin B phosphotransferase gene and its expression in *Escherichia coli* and *Saccharomyces cerevisiae*. *Gene*, 25 (2-3), 179-187. https://doi.org/10.1016/0378-1119 (83) 90223-8

Guilmanov, V., Ballistreri, A., Impallomeni, G., & Gross, R. A. (2002). Oxygen transfer rate and sophorose lipid production by *Candida bombicola*. *Biotechnology and Bioengineering*, 77 (5), 489-494. https://doi.org/10.1002/bit. 10177

Huang, F. C., Peter, A., & Schwab, W. (2014). Expression and characterization of CYP52 genes involved in the biosynthesis of sophorolipid and alkane metabolism from *Starmerella bombicola*. *Applied and Environmental Microbiology*, 80 (2), 766-776. https://doi.org/10.1128/AEM. 02886-13

Lang, S., Brakemeier, A., Heckmann, R., Spöckner, S., Rau, U., Spockner, S., & Rau, U. (2000). Production of native and modified sophorose lipids. *Chimica Oggi—Chemistry Today*, 18 (10), 76-79.

Lodens, S., De Graeve, M., Roelants, S. L. K. W. L. K. W., De Maeseneire, S. L. L., & Soetaert, W. (2018). Transformation of an exotic yeast species into a platform organism: a case study for engineering glycolipid production in the yeast *Starmerella bombicola*. P. in J. Braman Ed. Synth. Biol. Springer Publishing Co. Series "*Methods in Molecular Biology.,*" 1772, 95-123. https://doi.org/10.1007/978-1-4939-7795-6

Petersen, B. O., Vinogradov, E., Kay, W., Würtz, P., Nyberg, N. T., Duus, J., & Sørensen, O. W. (2006). H2B C: A new technique for NMR analysis of complex carbohydrates. *Carbohydrate Research*, 341 (4), 550-556. https://doi.org/10.1016/j.carres.2005.11.020

Rau, U., Hammen, S., Heckmann, R., & Wray, V. (2001). Sophorolipids: a source for novel compounds. *Industrial Crops and Products*, 13, 85-92.

Roelants, S. L. K. W. K. W., Ciesielska, K., De Maeseneire, S. L., Moens, H., Everaert, B., Verweire, S., . . . . Soetaert, W. (2016). Towards the industrialization of new biosurfactants: Biotechnological opportunities for the lactone esterase gene from *Starmerella bombicola*. *Biotechnology and Bioengineering*, 113 (3), 550-559. https://doi.org/10.1002/bit.25815

Roelants, S. L. K. W., Saerens, K. M. J., Derycke, T., Li, B., Lin, Y. -C., Van de Peer, Y., Soetaert, W. (2013). *Candida bombicola* as a platform organism for the production of tailor-made biomolecules. *Biotechnology and Bioengineering*, 110 (9), 2494-2503. https://doi.org/10.1002/bit.24895

Saerens, K. M. J. (2012). *Synthesis of glycolipids* by *Candida bombicola*. Retrieved from http://lib.ugent.be/catalog/rug01:001796661

Saerens, K. M. J., Saey, L., & Soetaert, W. (2011). One-step production of unacetylated sophorolipids by an acetyltransferase negative *Candida bombicola*. *Biotechnology and Bioengineering*, 108 (12), 2923-2931.

Soetaert, W., Van Bogaert, I., & Roelants, S. (2013). Methods to produce bolaamphiphilic glycolipids. WO 2015028278 A1. 50p.

Takahashi, F., Igarashi, K., & Hagihara, H. (2016). Identification of the fatty alcohol oxidase FAO1 from *Starmerella bombicola* and improved novel glycolipids production in an FAO1 knockout mutant. *Applied Microbiology and Biotechnology*, 100 (22), 9519-9528. https://doi.org/10.1007/s00253-016-7702-6

Van Bogaert, I. N. A., Buyst, D., Martins, J. C., Roelants, S. L. K. W. K. W., & Soetaert, W. K. (2016). Synthesis of bolaform biosurfactants by an engineered *Starmerella bombicola* yeast. *Biotechnology and Bioengineering*, 113 (12), 2644-2651. https://doi.org/10.1002/bit.26032

Van Bogaert, I. N. A., Holvoet, K., Roelants, S. L. K. W., Li, B., Lin, Y. -C. C., Van de Peer, Y., & Soetaert, W. (2013). The biosynthetic gene cluster for sophorolipids: a biotechnological interesting biosurfactant produced by *Starmerella bombicola*. *Molecular Microbiology*, 88 (3), 501-509. https://doi.org/10.1111/mmi.12200

Van Bogaert, I. N., Roelants, S., Develter, D., & Soetaert, W. (2010). Sophorolipid production by *Candida bombicola* on oils with a special fatty acid composition and their consequences on cell viability. *Biotechnology Letters*, 32 (10), 1509-1514. https://doi.org/10.1007/s10529-010-0323-8

Van Renterghem, L., Roelants, S. L. K. W., Baccile, N., Uyttersprot, K., Taelman, M. C., Everaert, B., . . . . Soetaert, W. (2018). From lab to market: An integrated bioprocess design approach for new-to-nature biosurfactants produced by *Starmerella bombicola*. *Biotechnology and Bioengineering*, 115 (5), 1195-1206. https://doi.org/10.1002/bit.26539

The invention claimed is:
1. A method to produce fully symmetrical bola sophorosides which are free of contaminating fatty acid-containing sophorolipids comprising feeding a mutated fungal strain with a fatty alcohol having an aliphatic tail chain length of at least 6 carbons,
wherein said fungal strain has a dysfunctional CYP52M1 cytochrome P450 monooxygenase and a dysfunctional FAO1 fatty alcohol oxidase, and
wherein said fungal strain is *Starmerella* (*Candida*) *bombicola* or a sophorolipid-producing strain of the *Starmerella* clade.

2. The method according to claim 1, wherein the gene encoding for the CYP52M1 cytochrome P450 monooxygenase and the gene encoding for the FAO1 fatty alcohol oxidase are knocked-out.

3. The method according to claim 1, wherein said fatty alcohol having an aliphatic tail chain length of at least 6 carbons is hexanol, octanol, decanol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, isostearyl alcohol, oleyl alcohol, nonadecyl alcohol, arachidyl alcohol or a mixture thereof.

4. The method according to claim 1, wherein said symmetrical bola sophorosides are acetylated.

5. The method according to claim 1, wherein the fully symmetrical bola sophorosides which are free of contaminating acidic, lactonic or bola sophorosides.

6. The method according to claim 1, wherein said symmetrical bola sophorosides are part of mixture further comprising alkyl sophorosides.

7. A mutated fungal strain having a dysfunctional CYP52M1 cytochrome P450 monooxygenase and a dysfunctional FAO1 fatty alcohol oxidase, wherein said fungal strain is a yeast selected from the group consisting of *Starmerella (Candida) bombicola*, or a sophorolipid-producing strain of the *Starmerella* clade.

8. A The mutated fungal strain according to claim 7, wherein said gene encoding for the CYP52M1 cytochrome P450 monooxygenase and said gene encoding for the FAO1 fatty alcohol oxidase are knocked-out.

9. A method to produce fully symmetrical terminal diols, said method comprising feeding the mutated fungal strain according to claim 7 with a fatty alcohol having an aliphatic tail chain length of at least 6 carbons to produce fully symmetrical terminal diols.

10. A method to produce alkyl sophorosides, said method comprising feeding the mutated fungal strain as defined in claim 7 with a fatty alcohol having an aliphatic tail chain length of at least 6 carbons to produce alkyl sophorosides.

11. A mutated fungal strain according to claim 7, wherein said fungal strain further comprises a dysfunctional glucosyltransferase UGTB1 that is responsible for the second glucosylation step in the sophorolipid biosynthetic pathway.

12. A method to produce symmetrical bola glucosides, said method comprising feeding the mutated fungal strain as defined in claim 11 with a fatty alcohol having an aliphatic tail chain length of at least 6 carbons to produce symmetrical bola glucosides.

13. The method according to claim 12, wherein said symmetrical bola glucosides are acetylated.

* * * * *